US010022439B2

(12) United States Patent
Dupont et al.

(10) Patent No.: US 10,022,439 B2
(45) Date of Patent: *Jul. 17, 2018

(54) ALLERGEN DESENSITIZATION METHOD

(71) Applicant: DBV TECHNOLOGIES, Bagneux (FR)

(72) Inventors: Christophe Dupont, Clamart (FR); Pierre-Henri Benhamou, Paris (FR); Bertrand Dupont, Aix en Provence (FR)

(73) Assignee: DBV Technologies, Montrouge (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,078

(22) Filed: Dec. 1, 2016

(65) Prior Publication Data

US 2017/0128566 A1    May 11, 2017

Related U.S. Application Data

(63) Continuation of application No. 12/745,870, filed as application No. PCT/FR2008/052199 on Dec. 3, 2008, now Pat. No. 9,539,318.

(60) Provisional application No. 61/084,305, filed on Jul. 29, 2008.

(30) Foreign Application Priority Data

Dec. 3, 2007 (FR) ..................... 07 59503

(51) Int. Cl.
*A61K 9/00* (2006.01)
*A61K 9/70* (2006.01)
*A61K 39/35* (2006.01)
*A61K 39/36* (2006.01)
*A61K 39/00* (2006.01)

(52) U.S. Cl.
CPC ............ *A61K 39/35* (2013.01); *A61K 9/0014* (2013.01); *A61K 9/7007* (2013.01); *A61K 39/36* (2013.01); *A61K 9/7023* (2013.01); *A61K 2039/54* (2013.01); *A61K 2039/545* (2013.01)

(58) Field of Classification Search
None
See application file for complete search history.

(56) References Cited

U.S. PATENT DOCUMENTS

| | | |
|---|---|---|
| 3,212,495 A | 10/1965 | Osbourn et al. |
| 3,645,852 A | 2/1972 | Axen et al. |
| 3,837,340 A | 9/1974 | Counter |
| 3,894,531 A | 7/1975 | Saunders, Jr. |
| 4,435,180 A | 3/1984 | Leeper |
| 4,450,844 A | 5/1984 | Quisno |
| 4,743,249 A | 5/1988 | Loveland |
| 4,781,705 A | 11/1988 | Shepherd et al. |
| 4,788,971 A | 12/1988 | Quisno |
| 4,821,733 A | 4/1989 | Peck |
| 4,836,217 A | 6/1989 | Fischer |
| 4,887,611 A | 12/1989 | Rudiger et al. |
| 5,230,898 A | 7/1993 | Horstmann et al. |
| 5,236,455 A | 8/1993 | Wilk et al. |
| 5,243,737 A | 9/1993 | Dainat |
| 5,423,737 A * | 6/1995 | Cartmell ............... A61F 13/023 206/440 |
| 5,438,984 A | 8/1995 | Schoendorfer |
| 5,827,608 A | 10/1998 | Rinehart et al. |
| 5,910,306 A | 6/1999 | Alving et al. |
| 5,944,662 A | 8/1999 | Schoendorfer |
| 5,980,898 A | 11/1999 | Glenn et al. |
| 6,093,419 A | 7/2000 | Rolf |
| 6,142,954 A | 11/2000 | Anhauser et al. |
| 6,210,705 B1 | 4/2001 | Mantelle et al. |
| 6,316,598 B1 | 11/2001 | Van Dyke et al. |
| 6,350,609 B1 | 2/2002 | Morozov et al. |
| 6,440,465 B1 | 8/2002 | Meisner |
| 6,486,311 B1 | 11/2002 | Burks et al. |
| 6,787,313 B2 | 9/2004 | Morozov et al. |
| 6,797,276 B1 | 9/2004 | Glenn et al. |
| 6,800,849 B2 | 10/2004 | Staats |
| 6,864,480 B2 | 3/2005 | Staats |
| 6,925,390 B2 | 8/2005 | Staats |
| 6,969,850 B2 | 11/2005 | Staats |
| 7,037,499 B1 | 5/2006 | Glenn et al. |
| 7,378,097 B2 | 5/2008 | Glenn et al. |
| 7,618,576 B2 | 11/2009 | Staats |

(Continued)

FOREIGN PATENT DOCUMENTS

| | | |
|---|---|---|
| EP | 0 107 832 A2 | 10/1983 |
| EP | 0 211 312 A1 | 2/1987 |
| EP | 0 252 044 A1 | 1/1988 |
| EP | 0 315 670 B1 | 5/1989 |
| EP | 0 409 465 A2 | 1/1991 |
| EP | 0 842 647 A1 | 5/1998 |
| EP | 0976396 A1 | 2/2000 |
| EP | 1 031 346 A1 | 8/2000 |
| EP | 1 356 821 A2 | 10/2003 |
| FR | 2 527 450 | 12/1983 |

(Continued)

OTHER PUBLICATIONS

Casadevall, Arturo et al., Passive Antibody Therapy for Infectious Diseases, Nature Reviews Microbiology, 2:695-703 (2004).
Cope, et al., "Effect of systemic antibody concentrations of topical application of choleratoxin to skin of sheep," Aust. Vet. J., (2000), 78(2):121-123.

(Continued)

*Primary Examiner* — Gigi Huang
(74) *Attorney, Agent, or Firm* — Foley & Lardner LLP; Christopher C. Bolten; Nicola A. Pisano

(57) ABSTRACT

The present application relates to a method for desensitization of allergic patients. More specifically it relates to an epicutaneous desensitization method, applicable to any type of allergens and of patients. The method of the invention is essentially non-invasive and does not require the use of adjuvants. Further, it may be easily applied and monitored by the actual patient.

14 Claims, 5 Drawing Sheets

(56) References Cited

U.S. PATENT DOCUMENTS

Figure 1:
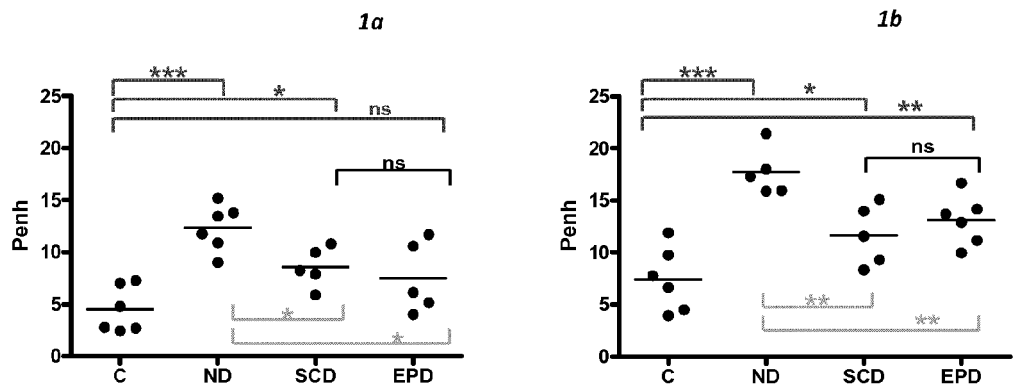

| | | | |
|---|---|---|---|
| 7,635,488 | B2 | 12/2009 | Dupont et al. |
| 7,722,897 | B2 | 5/2010 | Dupont et al. |
| 7,763,848 | B2 | 7/2010 | Staats et al. |
| 8,202,533 | B2 | 6/2012 | Mondoulet et al. |
| 8,287,899 | B2 | 10/2012 | Dupont |
| 8,932,596 | B2 | 1/2015 | Benhamou et al. |
| 8,968,743 | B2 | 3/2015 | Ronco et al. |
| 9,539,318 | B2 * | 1/2017 | Dupont ................ A61K 9/0014 |
| 2002/0061315 | A1 | 5/2002 | Kundig et al. |
| 2002/0102291 | A1 | 8/2002 | Mantelle et al. |
| 2002/0151487 | A1 | 10/2002 | Nickoloff et al. |
| 2002/0168761 | A1 | 11/2002 | Gour et al. |
| 2003/0064088 | A1 | 4/2003 | Carvalho et al. |
| 2004/0028727 | A1 | 2/2004 | Glenn et al. |
| 2004/0047902 | A1 * | 3/2004 | Dupont .............. A61B 10/0035 424/449 |
| 2004/0137004 | A1 | 7/2004 | Glenn et al. |
| 2004/0247622 | A1 | 12/2004 | Watson et al. |
| 2006/0002949 | A1 | 1/2006 | Glenn et al. |
| 2006/0147509 | A1 | 7/2006 | Kirkby et al. |
| 2007/0048361 | A1 | 3/2007 | Dupont et al. |
| 2007/0088248 | A1 | 4/2007 | Glenn et al. |
| 2008/0004564 | A1 | 1/2008 | Smith |
| 2008/0006769 | A1 | 1/2008 | Staats |
| 2009/0013648 | A1 | 1/2009 | Mastio et al. |
| 2009/0092635 | A1 | 4/2009 | Clarke et al. |
| 2009/0136480 | A1 | 5/2009 | Glenn et al. |
| 2009/0169602 | A1 | 7/2009 | Senti et al. |
| 2009/0214621 | A1 | 8/2009 | Dupont et al. |
| 2010/0136093 | A1 | 6/2010 | Mondoulet et al. |
| 2010/0222753 | A1 | 9/2010 | Dupont et al. |
| 2010/0297213 | A1 | 11/2010 | Dupont et al. |
| 2010/0310596 | A1 | 12/2010 | Ronco et al. |
| 2011/0206659 | A1 | 8/2011 | Penn |
| 2012/0064144 | A1 | 3/2012 | Benhamou et al. |
| 2013/0039958 | A1 | 2/2013 | Siegrist et al. |

FOREIGN PATENT DOCUMENTS

| | | |
|---|---|---|
| FR | 2 866 553 | 8/2005 |
| GB | 501873 | 3/1939 |
| GB | 1013895 | 12/1965 |
| JP | 06-238008 | 8/1994 |
| JP | 2000-083580 | 12/1999 |
| WO | WO-86/01994 | 4/1986 |
| WO | WO-90/00064 | 1/1990 |
| WO | WO-91/03998 | 4/1991 |
| WO | WO-96/32142 | 10/1996 |
| WO | WO-98/20734 | 5/1998 |
| WO | WO-98/20863 | 5/1998 |
| WO | WO-98/25521 | 6/1998 |
| WO | WO-98/31315 | 7/1998 |
| WO | WO-98/58745 | 12/1998 |
| WO | WO-99/43350 | 9/1999 |
| WO | WO-00/43058 A1 | 7/2000 |
| WO | WO-00/61184 A1 | 10/2000 |
| WO | WO-2001/49302 A1 | 7/2001 |
| WO | WO-2001/91718 A2 | 12/2001 |
| WO | WO-2002/30281 A1 | 4/2002 |
| WO | WO-2002/071950 A1 | 9/2002 |
| WO | WO-2002/074325 A1 | 9/2002 |
| WO | WO-2002/076379 A2 | 10/2002 |
| WO | WO-2002/089717 A1 | 11/2002 |
| WO | WO-2002/093998 A2 | 11/2002 |
| WO | WO-2004-030696 A2 | 4/2004 |
| WO | WO-2004-052425 A2 | 6/2004 |
| WO | WO-2005/025548 A1 | 3/2005 |
| WO | WO-2006/003659 A2 | 1/2006 |
| WO | WO-2006/007366 A2 | 1/2006 |
| WO | WO-2006/044206 A2 | 4/2006 |
| WO | WO-2006/128981 A1 | 12/2006 |
| WO | WO-2007/059979 A2 | 5/2007 |
| WO | WO-2007/122226 A2 | 11/2007 |
| WO | WO-2007/123707 A1 | 11/2007 |
| WO | WO 2007122226 A2 * | 11/2007 ......... A61B 10/0035 |
| WO | WO-2008/104720 A2 | 9/2008 |
| WO | WO-2008/132358 A1 | 11/2008 |
| WO | WO-2009/050403 A2 | 4/2009 |
| WO | WO-2009/071599 A1 | 6/2009 |
| WO | WO-2009/080933 A1 | 7/2009 |
| WO | WO-2009/080934 A2 | 7/2009 |
| WO | WO-2009/095591 A1 | 8/2009 |
| WO | WO-2010/103116 A2 | 9/2010 |
| WO | WO-2011/026966 A2 | 3/2011 |
| WO | WO-2013/117519 A1 | 8/2013 |

OTHER PUBLICATIONS

Dioszeghy, et al., "A New Delivery System for Epicutaneous Immunotherapy Promoting Specific Antigen Uptake by Langerhans Cells," Clinical Immunology, (2010), 135:S93 (Abstract only).

Dioszeghy, et al., "Repeated Applications of Peanut Protein Extracts During Epicutaneous Immunotherapy Induce a Change of Cytokine Response from Th2 to Mixed TH2/TH1 in Sensitized Mice," Clinical Immunology, (2009), 131:S86 (Abstract only).

Dioszeghy, et al., Epicutaneous Immunotherapy Results in Rapid Allergen Uptake by Dendritic Cells through Intact Skin and Downregulates the Allergen-Specific Response in Sensitized Mice, Journal of Immunology, 186(10):5629-5637 (2011).

Dupont, et al., Cow's milk epicutaneous immunotherapy in children: A pilot trial of safety, acceptability, and impact on allergic reactivity, J Allergy Clin Immunol, 125(5):1165-1167 (2010).

Dupont, et al., Epicutaneous Immunotherapy in Severe Cow Milk Allergy: A Double Blind Pilot Trial, J Allergy Clin Immunol, 123(2):S183, Abstract 700, (2009).

Fentanyl Patch, Brand Name: Duragesic Patches, downloaded Jan. 7, 2007 (6 pages).

Frerichs, et al., "Controlled, single-step, stratum corneum disruption as a pretreatment for immunization via a patch," Vaccine, (2008), 26(22):2782-2787.

Glenn, et al., "Advances in vaccine delivery: transcutaneous immunisation," Expert Opin. Investig. Drugs, (1999), 8(6):797-805.

Halperin, et al., A Comparison of the Intradermal and Subcutaneous Routes of Influenza Vaccination with A/New Jersey/76 (Swine Flu) and A/Victoria/75: Report of a Study and Review of the Literature, Am J Public Health, 69(12):1247-1251 (1979).

Hammond, et al., "Transcutaneous immunization: T cell responses and boosting of existing immunity," Vaccine, (2001), 19(17-19):2701-2707.

International Search Report dated Jun. 22, 2009 in Int'l PCT Patent Appl No. PCT/FR2008/052199.

International Search Report dated Mar. 8, 2013 in Int'l PCT Patent Appl No. PCT/EP2013/052163.

International Search Report dated Jun. 29, 2011 in Int'l PCT Patent Application No. PCT/EP2011/055991.

Kaiserlian, et al., "Epicutaneous and transcutaneous immunization using DNA or proteins," Eur. J. Dermatol., (1999), 9(3):169-176.

McConnell, et al., "Adenovirus-based Prime-boost Immunization for Rapid Vaccination Against Anthrax," Molecular Therapy, (2007), 15(1):203-210.

Mishra, et al., "Development of novel fusogenic vesosomes for transcutaneous immunization," Vaccine, (2006), 24(27-28):5559-5570.

Mondoulet, et al., Epicutaneous immunotherapy on intact skin using a new delivery system in a murine model of allergy, Clinical & Experimental Allergy, 40(4):659-667 (2010).

Mondoulet, et al., In Mice Sensitized to Milk, Epicutaneous Immunotherapy Prevents Further Sensitization to Peanut or House Dust Mite, J Allergy Clin Immunol, 129(2):AB113, Abstract 431 (2012).

Murata, et al., The polarization of Th1/Th2 balance is dependent on the intracellular thiol redox status of macrophages due to the distinctive cytokine production, International Immunology, 14(2):201-212 (2002).

Partidos, et al., "Immunity under the skin: potential application for topical delivery of vaccines," Vaccine, (2003), 21(7-8):776-780.

(56) References Cited

OTHER PUBLICATIONS

Paul, et al., Noninvasive administration of protein antigens: transdermal immunization with bovine serum albumin in transfersomes, Vaccine Research, 4(3):145-164 (1995).

Paul, et al., Transdermal immunization with large proteins by means of ultradeformable drug carriers, Eur J Immunol. 25(12):3521-3524 (1995).

Polypropylene, retrieved from http://psic.ws/mactest/pp.htm, 2005, Polymer Science Learning Center, Department of Polymer Sciences, The University of Southern Mississippi (3 pages).

Rogers, et al., Peptide Dose, Affinity, and Time of Differentiation Can Contribute to the Th1/Th2 Cytokine Balance, The Journal of Immunology, 163:1205-1213 (1999).

Shibaki, et al., Induction of skewed Th1/Th2 T-cell differentiation via subcutaneous immunization with Freund's adjuvant, Experimental Dermatology, 11:126-134 (2002).

Shiver, et al., "Replication-incompetent adenoviral vaccine vector elicits effective anti-immunodeficiency-virus immunity," Nature, (2002), 415(6869):331-335.

Strid, et al., "Disruption of the stratum corneum allows potent epicutaneous immunization with protein antigens resulting in a dominant systemic Th2 response," Eur. J. Immunol., (2004), 34:2100-2109.

Woodland, et al., Jump-starting the immune system: prime-boosting comes of age, Trends in Immunology, 25:98-104 (2004).

Wu, et al., "Enhanced Breadth of CD4 T-Cell Immunity by DNA Prime and Adenovirus Boost Immunization to Human Immunodeficiency Virus Env and Gag Immunogens," J. Virol., (2005), 79(13):8024-8031.

Zhang, et al., "Topical application of *Escherichia coli* particles over-producing pathogen-derived antigens as a simple vaccination modality in compliance with evolutionary medicine," Infect. Disord. Drug Targets, (2008), 8(3):189-194.

Dai, "Allergens in Atopic Dermatitis", Clinic Rev Allerg. Immunol., 33:157-166 (2007).

Gavillet et al., Needle-free and adjuvant-free epicutaneous boosting of pertussis immunity: Preclinical proof of concept, Vaccine 33:3450-3455 (2015).

Glenn, et al., Transcutaneous immunization: T cell responses and boosting of existing immunity, Vaccine 19:2701-2707 (2001).

Mondoulet et al., Intact skin and not stripped skin is crucial for the safety and efficacy of peanut epicutaneous immunotherapy (EPIT) in mice, Clinical and Translational Allergy, 2(22):1-12 (2012).

O'Hagan et al., Novel Approaches to Pediatric Vaccine Delivery, Advanced Drug Delivery Reviews, 58 (2006) 29-51.

O'Hagan, et al., Novel Approaches to Pediatric Vaccine Delivery, Adv. Drug Deliv. Rev, 58(1):29-51 (2006).

Thomas, Respiratory and Humoral Immune Response to Aerosol and Intramuscular Pertussis Vaccine, J. Hyg., Camb., 74:233-236 (1975).

\* cited by examiner

ALLERGEN DESENSITIZATION METHOD

CROSS-REFERENCE TO RELATED APPLICATIONS

This application is a continuation of U.S. application Ser. No. 12/745,870, filed Jun. 2, 2010, which is a U.S. national stage filing under 35 U.S.C. § 371 of International Patent Application No. PCT/FR2008/052199, filed Dec. 3, 2008, which claims the benefit of U.S. Provisional Patent Application No. 61/084,305, filed Jul. 29, 2008, and French Patent Application No. 0759503, filed Dec. 3, 2007, the entire contents of each of which are incorporated by reference herein.

FIELD OF THE INVENTION

The present application relates to a method for desensitizing allergic patients. More specifically it relates to an epicutaneous desensitization method, applicable to any type of allergens and patients. The method of the invention is essentially non-invasive and does not require the use of adjuvants. Further, it may easily be applied and followed by the actual patient.

DESCRIPTION OF RELATED ART

Allergy occupies an increasingly large place in daily medical practice. It is a worldwide public health phenomenon classified as the fourth worldwide scourge by the WHO. In France, one Frenchman out of three is allergic and both respiratory and food allergy affects an increasing portion of the population of adults and children.

Desensitization is the technique according to which by administering minimal amounts of allergens it is possible to more or less suppress the allergic phenomenon. Since the beginning of the years 2000, it has been recognized by the WHO as the only method for basically treating allergy.

It is now established that desensitization affects the immune response towards allergens as soon its first steps (Tij et al., 2004), which means that it not only reduces the symptoms related to short term allergic reaction but also that it modifies the natural history of the allergic «disease» and that it prevents both occurrence of allergy to new allergens, but also progression of the symptomatology towards more severe clinical signs, such as for example the transformation of allergic rhinitis into asthma.

Immunotherapy has proved to be effective in patients affected with severe IgE-dependent allergy, sensitized to a restricted number of allergens.

Although the action mechanisms of treatments by immunotherapy are not yet well-known, the latter may act by:
- increase in the IgGs and in particular in IgG4 fractions, antibodies blocking in vitro the biological effects of the IgEs, even if the significance of these effects in vivo still has to be evaluated,
- alteration of the TH1/TH2 balance, promoting TH1 response,
- production of T cells producing interleukin 10 (IL-10). The latter has many anti-allergic properties against mastocytes, certain T lymphocytes and eosinophilics and also promotes the production of IgG4.

Immunotherapy via a subcutaneous route represents for most allergologists the standard route and it is still widely used. Although costly and requiring the intervention of a specialist physician at each injection, it is today still considered as the standard desensitization route in children (Pajno et al., 2005). However it is not without risks, since the frequency of deaths is estimated to be 1 for 2.5 million injections with an average of 3.4 deaths per year.

Certain anaphylactic allergens with a high risk of reaction are not used within the scope of subcutaneous desensitization cures. This is the case of groundnuts and of most food allergens.

Sublingual immunotherapy is now considered by the WHO as a satisfactory alternative to immunotherapy via a subcutaneous route. It is being evaluated in many countries.

The first commercial preparations of tablets to be administered under the tongue, intended for a wide public are being sold in certain European countries and are being pre-marketed in the United States.

Much better tolerated by the patients, sublingual immunotherapy is for many authors, of a better cost-effectiveness ratio than the other routes of administration since it does not require the intervention of a physician and may be self-administered by the patients which admit that they prefer it to the other routes (Pajno et al., 2005).

Adverse reactions are rare during treatments via a sublingual route, estimated to be from 0.1 to 0.2 reactions for 1,000 administered doses. The reactions are mainly minor, affecting the buccal cavity or the sublingual area or the gastro-intestinal sphere (La Rosa et al., 1999).

In terms of effectiveness, the sublingual route is however considered by certain persons as less effective than the subcutaneous route; it requires the use of a larger amount of allergen and cannot be authorized with all allergens even if tests via this route for desensitization to groundnuts and to cow milk are in progress. The safety of the use of this technique with food allergens remains to be evaluated.

Intra-nasal immunotherapy has proved to be effective in 17 controlled studies out of 18. This is therefore an effective and safe route at the very least during allergic rhinitis. However, it is generally poorly tolerated by patients, which increasingly limits its clinical use. In a study comparing different desensitization routes, treatments via a nasal route were prematurely interrupted in close to 50% of the cases before one year, while early stopping only concerned less than 10% of the children treated via a subcutaneous or sublingual route (Pajno et al., 2005).

An advantageous alternative to these desensitization methods would lie in the possibility of carrying out immunotherapy via the epicutaneous route, i.e. by repeated application of an allergen on the skin, typically leading to diffusion of the allergen in the surface layers of the skin, generally without any significant transcutaneous passage.

It has been demonstrated for a long time in animals that repeated application of an allergen on the skin is capable of causing sensitization of the animal to said allergen (Golovanoff, 1926). The obtained reaction is of the systemic type and affects the body in its whole and therefore well beyond the simple cutaneous sphere.

More recently, models of mice sensitized to cow milk via an epicutaneous route have been developed (Chang). It has been shown that in these cases, the elicited immune response involves different cell populations and results in the activation of TH2 lymphocytes, which promote the production of specific IgE type antibodies of the allergen.

Certain investigations were able to establish that if the spontaneous response of the skin under stimulation conditions was actually of the TH2 type, it was possible to modify the immune profile of the response by subjecting the skin to different stimuli:
- Aggressions by physical agents such as ultraviolet rays
- Mechanical aggression of the skin by repeated strippings modifying the structure of the corneal layer
- Aggression by microbial agents such as choleric toxin
- Modification of skin permeability.

The type of immune response to the contact of an allergen may be modified by these different agents and results in preferential activation of TH1 lymphocytes promoting the production of antibodies of the IgG4 type.

The epicutaneous route was used by allergologists during the 50ies. It consisted of carrying out scarification on the skin through a drop of allergen several times a week (Pautrizel et al., 1957). Carried out by an experienced allergologist, this technique provided effectiveness and safety. However, carried out on a very small scale, and not very standardized, it has remained not very widespread. Finally, the hardship generated by repeated scarifications often very extended and mutilating is undoubtedly the reason why this method is abandoned today.

Patent application EP 1031346 proposes a vaccine containing a transdermal device and an antigen or allergen in order to obtain desensitization and application WO 2007/122226 mentions the use of a cutaneous device for desensitizing an allergic subject.

SUMMARY OF THE INVENTION

The present invention lies in the development of an effective epicutaneous desensitization method and with which the drawbacks and limits of the prior technique may be overcome.

More specifically, the invention partly lies on the demonstration that the specific inflammatory response caused by cutaneous application of allergens largely influences and participates in the reaction of immune cells in the sense of tolerance.

The invention consists of applying an allergen in a repeated and prolonged way on the skin so as to cause an inflammatory reaction, the profile of which oriented by the duration and the repetition of the applications is of the «tolerogenic» type. Thus, the invention is not only directed to eliciting the inflammatory reaction but also to orienting it.

The present application shows that controlling this inflammatory reaction conditions the obtained degree of tolerance and represents an essential element of the epicutaneous desensitization process. The invention shows that repeated elicitation of this specific inflammatory reaction is important for gradually inverting the immune response in the sense of tolerance, and it makes epicutaneous desensitization possible, even in the absence of any adjuvant or pre-treatment of the skin.

The invention thus proposes for the first time, a cutaneous desensitization method comprising repeated cutaneous application of an allergen on the skin of a subject under conditions allowing the inflammation generated by the application of the allergen on the skin to be sustained during the treatment. Advantageously, the method comprises at least one step for monitoring and/or evaluating the degree of the inflammation generated by the application of the allergen on the skin, the elicitation, sustainment and/or control of this reaction giving the possibility of directing the reaction of the body to the allergen in the sense of tolerance.

An object of the invention thus lies in the use of an allergen for preparing a composition for epicutaneous desensitization of a subject allergic to said allergen, by repeated applications of the allergen on the skin of a subject, characterized in that the allergen is applied on the skin under conditions allowing an inflammatory reaction to be sustained during the treatment. The invention indeed shows that sustainment of this inflammatory reaction promotes a response of the tolerogenic type from the immune system towards the allergen.

Another object of the invention lies in the use of an allergen for preparing a composition for epicutaneous desensitization of a subject allergic to said allergen, by repeated applications of the allergen on the skin of a subject, characterized in that it comprises during the treatment, preferably during each application of the allergen, a step for controlling and/or sustaining the inflammatory reaction generated by the application of the allergen on the skin.

Another object of the invention lies in the use of an allergen for preparing a composition for epicutaneous desensitization of a subject allergic to said allergen, by repeated applications of the allergen on the skin of a subject, characterized in that it comprises during the treatment, control and sustainment of the inflammatory reaction generated by the application of the allergen on the skin.

Another object of the invention lies in the use of an allergen for preparing a composition for modifying in the sense of tolerization the immune response of a subject allergic to said allergen, comprising repeated application of the allergen on the skin of a subject under conditions allowing sustainment of an inflammatory reaction during the treatment.

The invention further relates to an epicutaneous desensitization method of a subject allergic to an allergen, by repeated application of the allergen on the skin of a subject, characterized in that the allergen is applied on the skin under conditions allowing sustainment of an inflammatory reaction during the treatment.

As this will be described in details subsequently in the application, the inflammatory reaction is advantageously sustained by controlling or modulating during the treatment the dose or the frequency or the application time of the allergen, and/or its nature.

Another object of the invention lies in an epicutaneous desensitization method of a subject allergic to an allergen, characterized in that it comprises at least one step for evaluating during the treatment the degree of the inflammation generated by the application of the allergen on the skin. By evaluating the degree of the inflammatory reaction, the conditions of desensitization may be adjusted if necessary.

The invention further relates to a method for desensitizing a subject allergic to an allergen, by repeated applications of the allergen on the skin of a subject, characterized in that it comprises, at each application of the allergen, a step for controlling the inflammatory reaction.

The invention further relates to a method for desensitizing a subject allergic to an allergen, by repeated application of the allergen on the skin of a subject, characterized in that it comprises sustainment, during the treatment, of the inflammatory reaction generated by the application of the allergen on the skin.

The invention also relates to the use of the inflammatory reaction generated by the application of an allergen on the skin of a patient as a marker in order to adapt the treatment of said patient for epicutaneous desensitization to said allergen.

As this will be described subsequently in the application, the invention is applicable to any type of allergen and may be applied with any cutaneous application device. It allows effective desensitization without it being necessary to treat the skin of the patient beforehand. Moreover, it does not require co-administration of adjuvant compounds.

The use of allergen deposited on the skin of an allergic subject is perfectly safe, as demonstrated by the cumulated experience in the diagnostic field with the atopy patch test. In our experience in France with Diallertest®, a first ready-to-use atopy patch test marketed since 2004, no adverse effect has been reported, whether this is a severe local action or a generalized reaction of the systemic type.

After application of an allergen on the skin, the immune system may either not react or react with local (cutaneous) inflammatory reaction of a systemic immune reaction.

In a particular embodiment of the invention, the application of an allergen on the skin of a subject allergic to said allergen induces a cutaneous reaction, in particular of the inflammatory type, triggered by the contact of the allergen with keratinocytes and Langerhans cells present at the surface of the skin.

During epicutaneous immunotherapy by the method of the invention, this reaction caused by the application of the allergen on the skin of a subject allergic to said allergen is sustained and/or controlled during the cure. The invention indeed shows that sustainment and control of this reaction result in gradual orientation of the immune response in the sense of tolerance of the subject to said allergen. This response is clinically materialized by a gradual reduction or complete extinction of the cutaneous reactivity and by an increase in the tolerance threshold to said allergen.

The mechanism stated above applies to any allergen, notably to allergens acting on the digestive sphere (food allergy, such as to ovalbumin, groundnuts, shellfish, etc.), on the pulmonary sphere (respiratory allergy such as for example to pollen) or the cutaneous sphere.

Thus, the principle on which the method of the invention is based and which is perfectly illustrated by the experimental data discussed hereafter, is that it is possible to induce via a cutaneous route, tolerance of a subject previously sensitized to an allergen. This effect is obtained by maintaining the allergen on the skin of the subject allergic to said allergen and by doing this, causing, sustaining and controlling the inflammatory reaction to the allergen with the purpose of directing the reaction of the body to the allergen in the sense of tolerance.

Thus, the epicutaneous immunotherapy method of the invention is a therapeutic method for allergy which consists of putting immune cells of the skin (e.g. Langerhans cells, mastocytes, macrophages, leukocytes) in contact with an allergen in a subject allergic to said allergen and of eliciting via the specific, controlled and sustained cell inflammatory reaction, a conversion of the immune response resulting in tolerance to said allergen by the allergic patient. In the method of the invention, and unlike all the prior approaches to desensitization, the desensitization process is monitored and guided by the nature and the degree of the inflammatory reaction of the patient This approach provides effective desensitization adjustable to the needs and to the characteristics of each patient, and does not require the use of adjuvant compounds or preliminary perforating or abrasive treatment of the skin.

DETAILED DESCRIPTION

The method of the invention generally comprises application in a repeated, prolonged and controlled way of an allergen on the skin of a subject allergic to said allergen, under conditions (for example dose and/or frequency and/or application time conditions) allowing sustainment of an inflammatory reaction specific to the allergen during the treatment. In an advantageous embodiment, the application is accomplished without any adjuvant compound and/or on a healthy skin.

The method of the invention generally comprises the following phases:
  a. optional selection of the patients and/or the allergen (dose, nature, formulation, etc.);
  b. application of the allergen to the patient; and
  c. control of the inflammatory reaction; steps b. and c. being advantageously repeated one or several times during the treatment, the condition of the allergen (dose, nature, formulation, application frequency, exposure time, etc.) being adapted during the treatment in order to sustain the inflammatory reaction.

Insofar that the invention is based on the control of the inflammatory reaction, it is important that allergic patients subject to the treatment have such a response during the first application of the allergen on the skin. For this, the patient is advantageously subject to a first application (series) of the allergen, so as to determine the allergen preparation giving the most suitable reactivity at the beginning of the treatment.

For this purpose, the patient is advantageously subject to a first application of the allergen, in a predefined form and single dose.

If the subject develops a suitable inflammatory reaction, the treatment may be engaged on the basis of this allergen dose/form. A suitable reaction for example refers to an inflammation reaction visible to the naked eye, typically as infiltrated erythematous lesions either provided or not with papules or assuming an eczematiform aspect.

If the ascertained reaction is of strong intensity, including vesicles or even phlyctena, or is widely disseminated in neighboring skin areas or is strongly pruriginous, the allergen concentration for initiating the cure will be reduced, in order to obtain a suitable response or alternatively the application time of the allergen on the skin will be reduced.

On the contrary, when the ascertained reaction is of too low intensity, the allergen doses and/or the application time and/or the number of devices applied simultaneously, will be increased in order to obtain an initial significant reaction as defined above. In this case, it is also possible to test other forms of the allergen, in order to identify preparations giving better reactivity of the subject. Thus, indeed, the allergen may exist under different forms (complete foodstuff, protein extract, peptides, recombinant or synthetic products, etc.) which may elicit a different inflammatory response in allergic patients. This first phase of the treatment may thus allow determination of the most suitable form of the allergen for the beginning of the cure.

In this respect, in a particular embodiment, the patient is subject at the initial time of the cure to a series of devices containing various concentrations and/or forms of the allergen. With this first treatment it is possible to determine the dose and/or the optimum form, on a patient basis, being used as a reference for initiating the cure. If necessary, the use of these devices with various concentrations and/or forms may be repeated during the cure so as to adapt the dose/form used during treatment, depending on the change in reactivity of the subject.

When the initial dose/form has been determined, the epicutaneous immunotherapy treatment may be engaged. This treatment comprises repeated application of the allergen on the skin. The application is advantageously carried out at the upper portion of the back of the subject or on the inner face of the arms or forearms. It may also be carried out on any other region of the body, under the preferential condition that the local reactivity to the allergen has been checked beforehand. It is understood that, during the treatment, the allergen may be applied on different regions of the body. The applications are renewed at a variable frequency, depending on the therapeutic procedure used (a typical procedure comprises an initial application time comprised between about 6 and 72 hrs). They may be applied continuously or batchwise while observing variable time intervals between the applications (which may range from 1 day to three weeks, for example). Repeated and prolonged application for several months of the allergen results in local release of mediators of the inflammation and in the inflow of inflammatory cells which influence the reaction of the immune cells in the sense of tolerance. A typical procedure comprises repeated application of the allergen, for periods from about 6 to 72 hrs, spaced out by about 5-15 d, over a period required for desensitizing the subject, this period may exceed several months.

In order to ensure suitable desensitization, the present invention demonstrates that it is important to control and sustain (by modulating the doses and/or the times or frequency of exposure to the allergen, or its form), a local inflammation reaction during the treatment. The method of the invention thus comprises regular evaluation of the degree of the inflammation generated by repeated application of the allergen on the skin. Thus, during the cure, the allergen doses and/or the period, and/or the number of devices used simultaneously, will be adapted depending on the degree of the cutaneous reactivity. A decrease in the intensity of the cutaneous reaction during the treatment results in an increase in the application frequency and/or in the number of devices applied simultaneously and/or in the dose of the allergen, and/or in a modification of its form. On the contrary, an increase in the intensity of the cutaneous reaction results in a reduction of the application frequency and/or of the number of devices applied simultaneously and/or of the concentration of the allergen in said device, and/or of its form.

The evaluation of the intensity of the inflammatory reaction, in particular of the cutaneous reaction, may be carried out by the physician and/or by the actual patient. This evaluation may be carried out by any method, conveniently by visual examination or by contact, for example by using the consensual assessment grid of the EAACI (see Allergy 61 (2006) 1377-1384). Thus, there exist different degrees in the cutaneous inflammatory reaction: erythema-erythema and infiltrations-erythema and a few papules-erythema provided with many papules-erythema with vesicles. A suitable inflammatory reaction is typically an inflammatory reaction of type III, i.e. comprising erythema and a few papules. As far as possible, this is the type of reaction which one attempts to sustain during the treatment. Of course, when the patient develops a less strong reaction from the start, the reference reaction will necessarily be less strong, and it will be adapted on a patient basis. Moreover, during the treatment, the inflammatory reaction will decrease because of the desensitization of the subject.

For applying the invention, it is also possible to evaluate the inflammatory reaction by dosing inflammation markers, such as cytokines or interferons.

In order to adjust the treatment as best as possible, in a particular embodiment of the invention, the inflammatory reactivity is evaluated one or several times during the treatment by putting the subject into contact with a range of doses of the allergen, allowing selection of the best adapted dose for continuation of the treatment.

The evaluation of the inflammatory reaction may be performed all along the treatment, i.e. at each new application of the allergen.

It is also possible to only perform this evaluation at certain intervals and not at each application.

Further, if it is preferred to sustain an inflammatory reaction all along the treatment, this is not mandatory and effective desensitization may also be obtained when the immune contact has been established a first time and when specific cascade reactions (activation of immunologically competent cells and production of cytokines and antibodies) have been sufficiently triggered. Thus, in practice, when the inflammatory reaction has reached a sufficient level, for example expressed by a cutaneous reaction of the intended intensity, it is possible to remove the device, and then after a delay to be defined, to put another one in another cutaneous area.

In an alternative of the invention, the allergen (or the application device) is maintained on the skin at least until the inflammatory reaction reaches a degree of reference. When this degree is reached, the allergen (or the device) may be removed, and a latency period is observed before a new application. The reference reaction is typically a reaction visible to the naked eye, for example as infiltrated erythematous lesions or having an eczematiform aspect.

The allergen (or the device) may also be maintained on the skin so as to sustain the inflammatory reaction. Typically, in this case, the application device is removed when all the allergen will have diffused, or if the inflammatory reaction reaches a too strong intensity.

It is understood that, during the treatment, these alternatives may be alternated.

In an embodiment, a period of time comprised between 1 and 21 days is left to elapse between the setting-up of devices.

The treatment may be considered as completed and successfully conducted when any cutaneous reactivity to the allergen will have disappeared or will have been reduced very significantly. The success of the cure may be confirmed by an oral elicitation test, or by any other means recognized in allergology. Accordingly, the duration of the cure is variable and depends on the evolution of the cutaneous reactivity to the allergen. The objective of the desensitization cure according to the method of the invention is either to cause the local cutaneous reaction to the allergen after prolonged contact to disappear entirely or to reduce the reactivity so that it is estimated that the reactivity of the subject to the allergen has been significantly reduced by the epicutaneous immunotherapy cure, the risk of anaphylactic shock during accidental contact with the allergen is significantly reduced.

The invention may be applied with any cutaneous administration device ensuring contact of the skin with the allergen. These are preferably devices of the patch type, patches or bandages, preferably patches, for example occlusive patches.

Such a device typically comprises a support on which the allergen is fixed, and/or a reservoir or a chamber comprising the allergen.

The device used is typically of transdermal nature with passive diffusion, i.e. it does not contain any means for causing perforation or abrasion of the skin. Indeed, the obtained data show that the method of the invention allows epicutaneous desensitization to be induced even without preliminary skin treatment. However, it is also possible to use a device provided with properties aiming at increasing the permeability of the surface layers of the skin to the allergen and/or at increasing the cutaneous reactivity with physical, chemical or biological means. Thus, in one alternative, the application device may act on the permeability by means of micro-needles or electric means promoting the passage of the allergen as far as the basal layer of the epidermis. Further, although this is not essential, it is possible to pre-treat the skin (for example by an abrasive treatment) before each application of the device in order to further promote the desensitization treatment.

In a preferred embodiment, a device of the occlusive patch type is used, such as for example an electrostatic patch Viaskin® described in patent application WO02/071950.

Moreover, in a preferred embodiment, the device is provided with means ensuring its maintaining on the skin. Any adhesive means may be used for this purpose, including materials of the gum, polymer or plastic type, having strong adhesivity. It is also possible to use a device provided with a bracelet, as described for example in application No. FR0753787, or with an exfoliation sheet, as described for example in application No. FR0753265.

It is understood that the specific nature and form of the device may be adapted by one skilled in the art, the required property being to ensure contact between the allergen and the skin at the application site.

In a particular embodiment, the treatment is performed by means of a device provided with an at least partly transparent backing (for example a VIASKIN® device), so that the inflammatory reaction (for example appearance of erythema) may be directly observed through the transparent membrane. The backing of the device may even be adapted in order to help the patient in determining the cutaneous reaction threshold level from which he/she will be able to remove the device. Thus, in a particularly advantageous embodiment, a device is used for which the backing has a transparent area on which is printed a monitoring pattern for example a red grid or red concentric circles. When the skin has not reacted, the drawings are well visible and they are erased when the cutaneous reaction is obtained. Resorting to a transparent backing system has many advantages, and notably:

- this avoids unnecessary prolonged contact with the allergen, improves cutaneous tolerance, minimizes unpleasant secondary effects of the prurit type and in fact improves acceptance and observance;
- this increases the performances of the method in terms of safety and further minimizes the risks of systemic reaction which have been fatal to many methods for desensitization to groundnuts in the past;
- this provides a solution with which the notion of variable exposure time to the allergen may be integrated into the industrial process.

In this context, an object of the invention relates to a cutaneous device for applying an allergen on the skin of a subject, characterized in that it comprises a backing provided with a transparent area through which the inflammatory cutaneous reaction elicited by the application of the allergen on the skin may be viewed. Advantageously, the device is a device of the occlusive type and/or with passive diffusion. The device is typically a patch.

Another object of the invention moreover relates to a kit comprising several devices for cutaneous application of an allergen, the devices comprising different doses of the allergen and/or different forms of the allergen.

The allergen used within the scope of the invention may be of various nature, form and origin. Thus, it may be a food, respiratory or cutaneous allergen, for example. These may be proteins (or polypeptides or peptides), lipids, sugars, etc., which may be in the form of extraction products, in a recombinant form, and/or of synthetic origin, for example if necessary, chemically or immunologically modified in order to modify their properties. The allergens may be in an entire, native form, or in a fragmented, denatured form, etc. A preparation is typically used, comprising several allergenic antigens as a combination, and/or allergen(s) as conjugates or complexes. It is understood that the method of the invention is essentially independent of the nature of the allergen, and may therefore be applied to any preparation comprising allergens, such as for example food allergens (e.g. groundnut, shellfish, milk, egg, fish, wheat, soya bean, etc.) or cutaneous or respiratory allergens (mites, pollen, animal hairs, etc.).

The allergen is advantageously formulated with any excipient or carrier adapted to pharmaceutical use. The applied allergenic preparation may appear in different forms, such as for example as a liquid or solid. In a preferred embodiment, the allergen is in dry form, i.e. in dehydrated form, and notably as a powder, particles, agglomerates, a wafer, dried form, etc. The dry form may be obtained by freeze-drying, of by simple evaporation.

In a particular embodiment, the allergen is in the form of a powder.

As indicated earlier, an advantage of the invention it that with it, it is possible to obtain desensitization to an allergen even without co-administration of an adjuvant. Also, in a preferred embodiment, the allergenic preparation applied on the skin of a patient, is free of any added adjuvant compound. The term adjuvant in the sense of the invention designates any compound which exerts physico-chemical and/or biological action on the skin, facilitating penetration of the antigen into the skin, and which increases the immune response against the antigen. By physico-chemical and/or biological action, the adjuvant, as defined here, is a compound which alters the permeability of the epidermis by disturbing the corneal layer, thereby allowing passage of the antigen and its contact with the immunologically active cells of the epidermis. Examples of adjuvant compounds are notably choleric toxin (CT) or thermolabile toxin (LT) of *E-coli*. Other examples are transfersomes, described by Paul et al. (Paul A, Cevc G, Bachhawat BK. Transdermal immunization with large proteins by ultradeformable drug carriers. Eur. J. Immunol. 1995, 25 (12): 3521-4), which allow transport of an antigen in the membranes.

Nevertheless, in one alternative, the allergen may be used as a combination with an adjuvant compound and/or provided with properties for amplifying the inflammatory reaction to said allergen, for example with adjuvants or compounds with immuno-modulating activity, such as for example a cytokine, a compound, Toll receptor ligands, etc. The expression «used as a combination» indicates that the allergen and the compound are administered to the same subject in order to induce a cooperation effect in vivo. Nevertheless, they may be administered according to various procedures and routes. Thus, they may be both applied via an epicutaneous route, or else the compound is applied via another route. Moreover, they are not necessarily applied at the same time, but may be applied sequentially, repeatedly or not, and at similar frequencies or not. Typically, the adjuvant compound is administered before or at the same time as the allergen.

In a normal embodiment, the device contains an amount of allergens comprised between 0.1 and 1,000 $\mu g/cm^2$ of the surface area of the device, preferably between 20 and 500 $\mu g$ per $cm^2$, more preferentially between 20 and 200 $\mu g$ per $cm^2$. It is understood that this amount may be adapted by one skilled in the art depending on the goals, the pathology, the duration of the treatment, the subject, etc.

The experimental examples which follow show that such a reduction in reactivity may be attained by using a control of the doses according to the invention. The epicutaneous immunotherapy method of the invention includes many advantages relatively to the present state of the art.

This is an original method aiming at eliciting and controlling an inflammatory reaction by regularly and durably applying an allergen on the skin of a subject allergic to said allergen with the purpose of directing the reaction of the body against this allergen towards tolerance.

This is a perfectly safe method as confirmed by cumulated experience in the field of atopy patch tests as well as by data collected since the introduction of the DIALLERTEST® in France, a first ready-to-use atopy patch test with more than 100,000 distributed copies. Because of this great safety of use, with the method according to the invention, it is possible to desensitize subjects allergic to allergens such as groundnuts or shellfish, which are not managed by standard desensitization methods because of the incurred risks.

Immunotherapy may be interrupted at any moment by removing the device applied on the skin, which cannot be contemplated with traditional desensitization methods during which the antigen is administered into the body.

With the first step of the method, it is possible to confirm eligibility of the subject for epicutaneous immunotherapy (the subjects having a cutaneous reaction are eligible) on the one hand, and to measure the degree of cutaneous reactivity of the subject to the allergen on the other hand, in order to at best guide the management of the epicutaneous immunotherapy cure. It is thus possible to select the procedure which is the most adapted to the patient in order to optimize cutaneous tolerance and to maintain the best level of effectiveness.

During the cure, it is possible to adjust the dosage and/or the frequency of administration depending on the evolution of the cutaneous reactivity, as measured continuously. It is thus possible to permanently optimize the therapeutic action and to maintain the highest level of effectiveness all along the treatment.

The duration of the cure depends on the therapeutic objectives set at the beginning of the cure and on the evolution of the cutaneous reactivity to the allergen. The cure is considered as completed when the objectives of reducing reactivity to the allergen as ascertained on the skin are achieved and confirmed by an elicitation test or any other allergology means or when complete extinction of cutaneous reactivity is ascertained.

Other aspects and advantages of the invention will become apparent upon reading the examples which follow, which should be considered as illustrative and non-limiting.

CAPTIONS OF THE FIGURES

FIG. 1: plethysmography results obtained after 8 weeks (a) or 16 weeks (b) for desensitization to the pollen of Dactyle. C: control, ND: non-desensitized, SCD: subcutaneous desensitization, EPD: epicutaneous desensitization.

Figure 2:
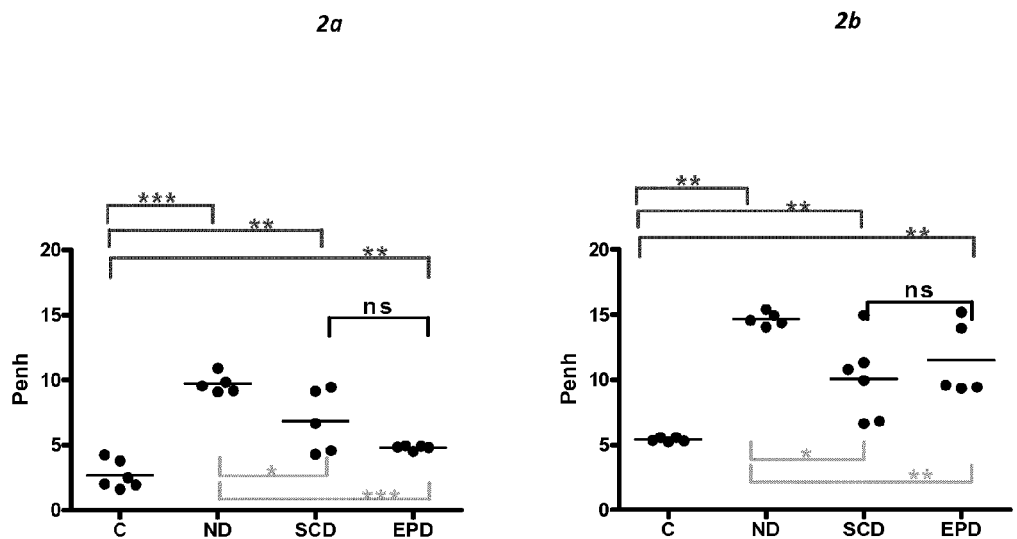

FIG. 2: plethysmography results obtained after 8 weeks (a) or 16 weeks (b) for desensitization to ovalbumin. C: control, ND: non-desensitized, SCD: subcutaneous desensitization, EPD: epicutaneous desensitization.

Figure 3:
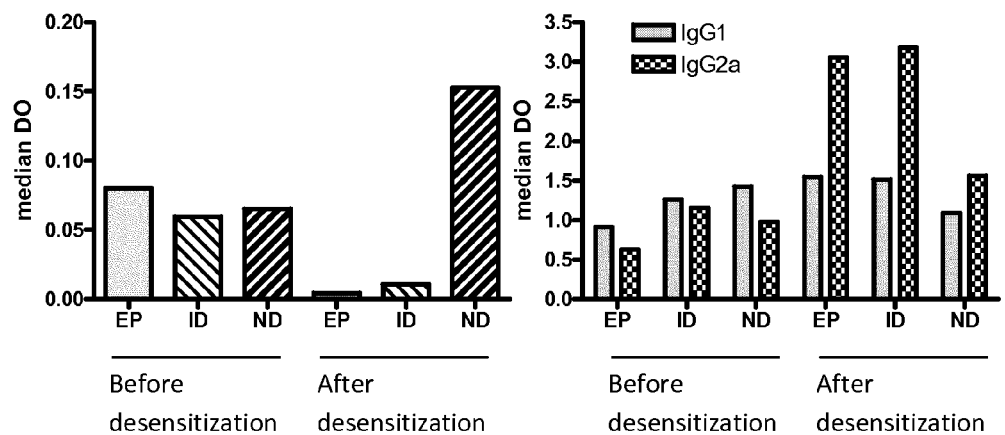

FIG. 3: monitoring of the antibody level before and after 8 weeks of desensitization with groundnut proteins. Left graph: IgE specific, right graph: IgG1 and IgG2a specific. EP: epicutaneous, ID: intradermal, ND: non-desensitized.

Figure 4:
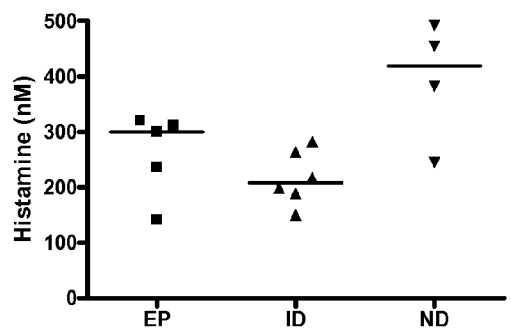

FIG. 4: histamine released after an elicitation test. EP: epicutaneous, ID: intradermal, ND: non-desensitized. The results are expressed in nM.

Figure 5:
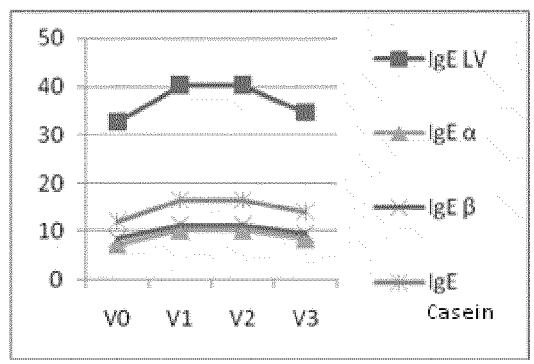

FIG. 5: evolution of the rate of specific IgEs (V0, initial sample, V1, samples at one month, V3, sample at 3 months).

Figure 6:
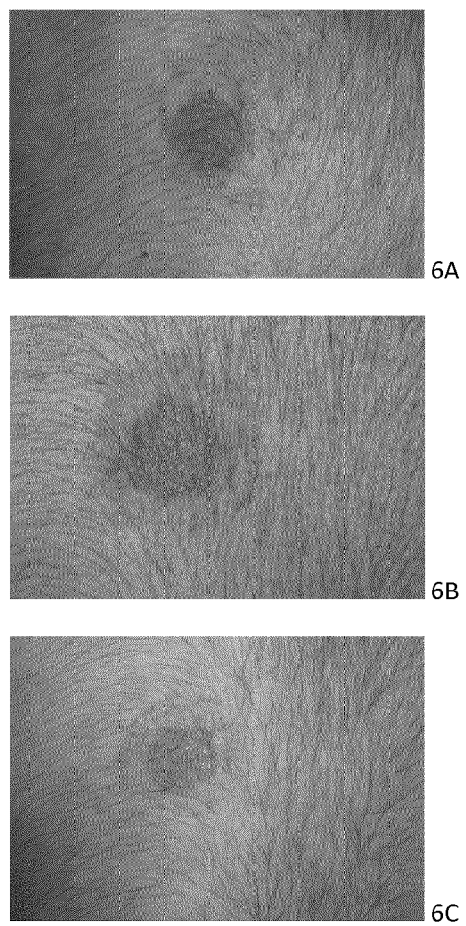

FIG. 6: viewing the cutaneous inflammatory reaction during the treatment: A: marked; B: medium; C: attenuated.

Figure 7A:
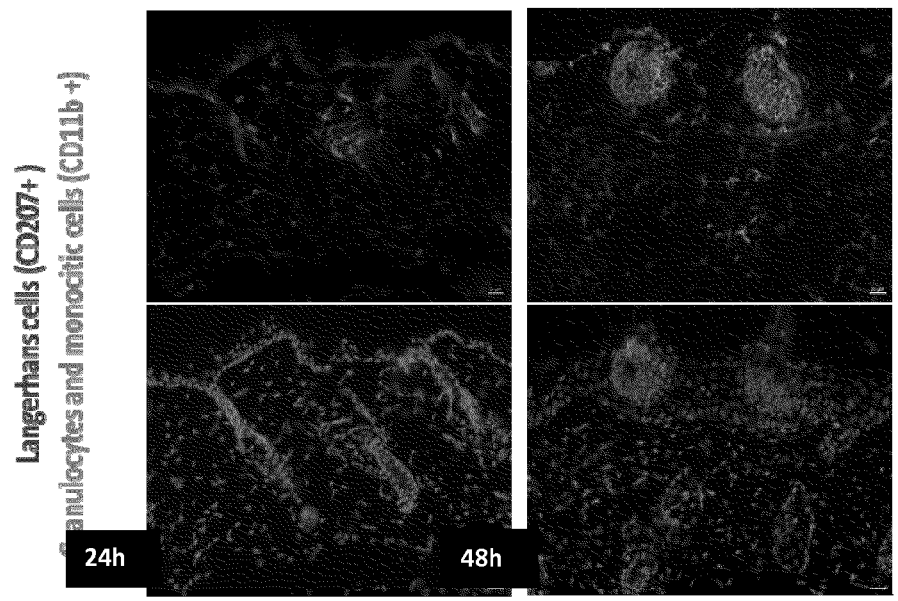

FIG. 7A: activation of Langerhans cells and inflow of inflammatory cells after 24 hrs and 48 hrs of application of an allergen with VIASKIN®. After 24 hrs of application, the Langerhans cells are activated and begin their migration towards the lymph nodes. After 48 hrs, the inflammatory cells are alerted and inflammatory granulomas are well visible.

Figure 7B:
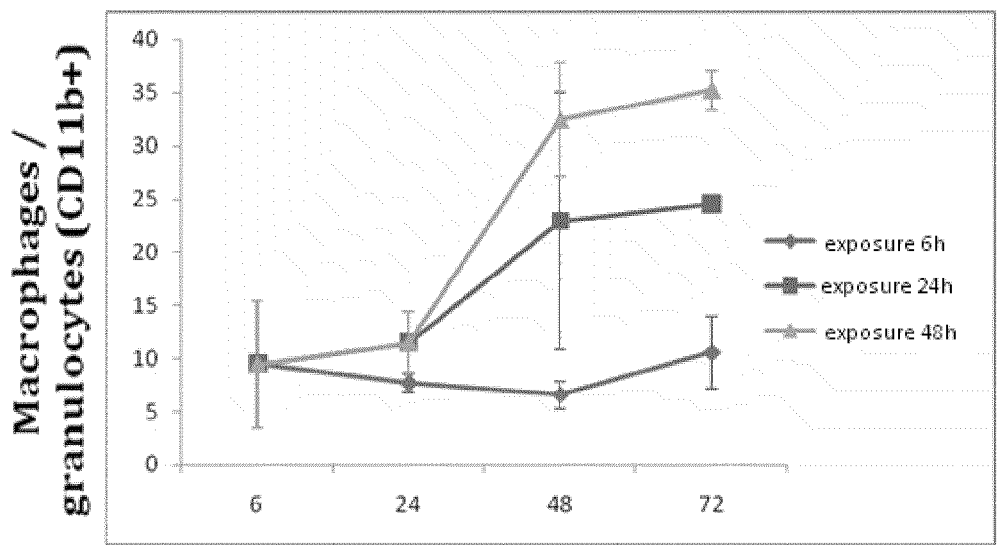

FIG. 7B: evolution of the local cell response after different application times of an allergen (ovalbumin) with VIASKIN®. After 6 hrs of application, the cell response is not perceptible. After 24 hrs, the rise in the local rate of inflammatory cells continues after removing VIASKIN®. This evolution is stronger after 48 hrs of application.

Figure 8:
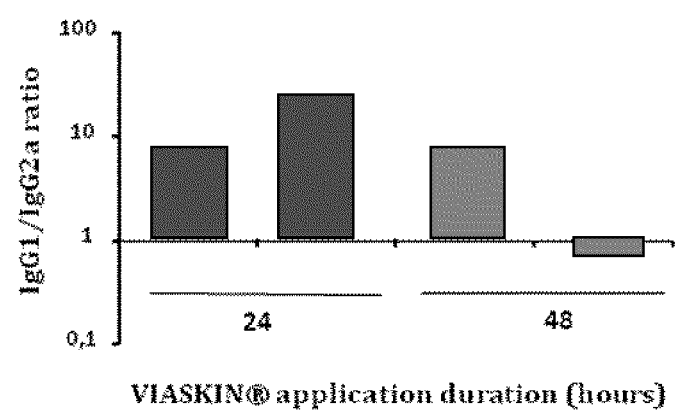

FIG. 8: evolution of the local response profile after prolonged application (6 and 12 weeks) of an allergen on the skin of an animal sensitized with VIASKIN®. After repeated application for 24 hrs, the response is predominantly of type TH2. After repeated applications for 48 hrs, the response is mixed, and then predominantly TH1.

EXAMPLES

Example 1. Desensitization to Ovalbumin and to Pollen 1.1. Methodology

In the case of OVA and POL, BALB/c mice were sensitized for 2 weeks in succession (D0 and D7) by subcutaneous injection of 10 µg of allergen associated with aluminium hydroxide. At D14, the mice received nasal instillation of 10 µg of allergen alone.

From D21, the mice either followed a desensitization treatment or not. The treated mice received once a week for 8 weeks, 100 µg of allergen administered either via an epicutaneous route by means of the VIASKIN® system, under conditions ensuring sustainment of the cutaneous inflammatory reaction, or via a subcutaneous route in association with aluminium hydroxide (positive control). The non-desensitized mice were maintained under normal conditions of an animal house.

The evolution of the antibody (IgE and IgG specific) levels was tracked on sera from ice, sampled after 8 weeks and 16 weeks of desensitization.

The effectiveness of OVA and POL desensitization treatment was also studied by plethysmography measurements allowing evaluation of bronchial hyperreactivity of mice either desensitized or not.

1.2. Results

Bronchial hyperreactivity was measured for mice either treated or not with VIASKIN® (FIGS. 1 and 2).

Bronchial hyperreactivity of the mice treated with VIASKIN® under conditions ensuring sustainment of the cutaneous inflammatory reaction, is significantly reduced, by 3.7 to 2.6 times relatively to untreated mice. Bronchial hyper reactivity of the mice treated subcutaneously is not significantly different from that of mice treated with VIASKIN®.

Example 2. Desensitization to Groundnuts 2.1. Methodology

For ARA (groundnuts), the mice were sensitized over 6 weeks by intragastric administration every 6 days (D1, D7, D13, D19, D25, D33) of 1 mg of ARA proteins associated with 10 µg of choleric toxin.

The desensitization procedure begins at D75 for a period of 8 weeks. The mice are desensitized once a week by administering 100 µg of ARA formulation via an intradermal route or via an epicutaneous route with the system VIASKIN®, under conditions ensuring sustainment of the inflammatory reaction. Non-desensitized mice do not follow any particular treatment after sensitization.

The effectiveness of desensitization is tracked by measuring the antibody (IgE, IgG1 and IgG2a specific) level as well as by measuring the release of histamine after oral elicitation tests. Histamine is a mediator released during degranulation of immune cells of the mastocytes or basophilic type. This degranulation is a marker of the induction of the allergic response.

2.2. Results

The analysis of the ARA desensitization treatment was validated by analysis of the specific antibody levels in mice (FIG. 3). The mice desensitized via an epicutaneous route or via an intradermal route have a reduction in the level of specific IgE (marker of allergy to ARA) and an increase in the specific IgG2a level. Specific IgE levels detectable in non-desensitized mice remain high and specific IgG2a levels are lower than in desensitized mice. No significant difference was observed between the epicutaneous and intradermal desensitization routes.

Oral elicitation tests were conducted on mice either desensitized or not. The mice desensitized via an intradermal route or via an epicutaneous route have lower release of histamine than non-desensitized mice. This result shows a decrease in the allergic reactivity of desensitized mice.

Discussion

Through the different study models and the different studied allergens, it appears that:
- the epicutaneous immunotherapy method based on sustainment of the inflammatory response enables triggering of a clinical and biological response of the systemic type;
- the animals having benefited from the epicutaneous immunotherapy method based on sustainment of the inflammatory response after preliminary sensitization via an oral or cutaneous route have an attenuated response to elicitation tests, comparable with that of animals having been subject to immunotherapy via a subcutaneous or intradermal route;
- the obtained serological response confirms induction of a tolerance process by epicutaneous immunotherapy.

Example 3. Clinical Data

Characteristic of the Patient:

child, 6 years 5 months old, 18.3 kg. Chronic diarrhea, vomiting, generalized eczema. Positive prick test to cow milk. Total IgE 486 IU. Cow milk specific IgE 32.7 IU.

Positive milk elicitation test at 0.6 mL (laryngeal prurit, coughing, abdominal pains, urticaria).

Treatment:

Application of VIASKIN® containing 130 µg of milk proteins, renewed every two days for 3 months under conditions ensuring persistence of a cutaneous reaction upon contact with the allergen.

Results:

The results are shown in FIGS. 5 and 6. They illustrate very substantial improvement in the tolerance threshold to cow milk, correlated with monitoring of the inflammatory reaction during the treatment. At the end of the immunotherapy cure, attenuation of the cutaneous reaction is ascertained. The oral elicitation test at 3 months shows a tolerance threshold up to 64.6 mL without any clinical reaction.

Example 4. Evolution of the Cell Response Following Application of an Allergen in Sensitized Mice Application of an allergen on the skin of the mouse sensitized beforehand activates Langerhans cells and their migration towards lymph nodes (FIG. 7A).

Within the same time, the activated cells produce pro-inflammatory cytokines which attract the cells of the inflammation towards the surface layer of the skin. This «first phase» reaction occurs in sensitized subjects since it has memory cells and specific IgEs directed against the allergen. Therefore, upon contact with the allergen, there occurs an initial reaction of rejection of the allergen.

In a second phase, a local inflammatory reaction characterized by the inflow of acute inflammation cells (mastocytes, macrophages) and chronic cells (leukocytes), appears (FIGS. 7A and 7B). In mice sensitized beforehand, application of an allergen (ovalbumin) on the skin with Viaskin® is expressed by a slightly inflammatory reaction after 24 hrs of contact and on the other hand by a massively inflammatory reaction after 24 hrs of contact with invasion of the cutaneous area by polynuclears. It is this more complex reaction which is targeted by the treatment.

In an investigation conducted in sensitized mice, the application of the allergen 6 hrs, 24 hrs and 48 hrs determines an inflammatory reaction (materialized here by local increase in the level of macrophages) which is more significant after 48 hrs of application (FIG. 7B).

Discussion

During the epicutaneous desensitization treatment, the aim is to reproduce an inflammatory cell reaction, the role of which is indispensable in the tolerance process.

In reality, it is not the intensity of the inflammatory reaction which varies over time but especially its very nature.

Immunofluorescence studies confirm the central role of the inflammation and the completely different aspect of the profile of the inflammatory reaction depending on the application time.

The application time of the allergen is an essential factor for eliciting a cell reaction.

Example 5. Evolution of the Local Response Profile after Prolonged Application of an Allergen The application time is not a sufficient condition for obtaining the type of sought therapeutic (tolerogenic) reaction. In mice, repeated administration of an allergen on the skin causes a rise in the specific antibodies of this allergen regardless of whether the application is «short» (24 hrs) or «long» (48 hs). When the application is continued (up to 88 days), the level of the antibodies is still also high but the relative proportion of Th1/Th2 lymphocytes is modified in the direction of a rise in Th1 lymphocytes in subjects receiving Viaskin® for 48 hrs (FIG. 8).

Discussion

Experimental data demonstrate that the method according to the invention is aimed at inducing a reaction, the characteristics of which are different from the reaction usually obtained by simply depositing the allergen on the skin of allergic persons. It is only the reaction obtained after «long» application by means of Viaskin®, with which a «tolerogenic» effect may be obtained, materialized by an activation of Th1 lymphocyte cells while the reaction obtained after a «short» application is of the Th2 type.

During the desensitization cure by Viaskin®, repeated application of the allergen on the intact skin of the patient sensitized beforehand, elicits an inflammatory cell reaction as currently observed clinically with atopy patch tests.

By eliciting and sustaining the inflammatory reaction by repeated and prolonged application of the allergen, specific local inflammation conditions are created. During this reaction, the equilibrium is shifted in favor of the Th1 lymphocytes.

It therefore appears that prolonged and repeated application of an allergen on the skin is not only capable of causing an inflammatory reaction, but also of orienting this reaction.

The invention claimed is:

1. A method for epicutaneous desensitization of a subject allergic to milk, the method comprising:
    a) determining a dose of a milk allergen which causes a local inflammatory reaction on the skin of the subject upon epicutaneous application thereof;
    b) epicutaneously exposing the subject to the milk allergen and generating the local inflammatory reaction in the subject by applying said dose of the milk allergen, without an adjuvant, onto an intact region of skin of the subject; and
    c) repeatedly applying the milk allergen, without an adjuvant, to an intact region of the skin of the subject, at a dose, frequency or for an application time adapted to sustain a local inflammatory reaction, the exposure and sustained reaction leading to desensitization of the subject;
    wherein the milk allergen is applied by a cutaneous occlusive device configured to ensure contact between the allergen and the region of skin, and wherein said dose of milk allergen is comprised between 0.1 and 1,000 µg/cm$^2$ of a surface area of the device.

2. The method of claim 1, further comprising visually evaluating the inflammatory reaction.

3. The method of claim 1, wherein the dose, frequency, or application time of the milk allergen is increased as the inflammatory reaction decreases during the repeated applications.

4. The method of claim 1, wherein the dose, frequency, or application time of the milk allergen is decreased as the inflammatory reaction increases during the repeated applications.

5. The method of claim 1, wherein the milk allergen is in powder form.

6. The method of claim 1, wherein the inflammatory reaction generated during the generating step is visible to a naked eye.

7. The method of claim 6, wherein the inflammatory reaction comprises an infiltrated erythematous lesion.

8. The method of claim 6, wherein the inflammatory reaction has an eczematiform aspect.

9. The method of claim 1, wherein the device comprises a transparent backing configured to allow the inflammatory reaction to be viewed.

10. The method of claim 9, wherein the backing comprises a grid configured to aid in an evaluation of the inflammatory reaction.

11. The method of claim 1, wherein the device is removable.

12. The method of claim 1, wherein step a) comprises determining the inflammatory reaction of the subject generated by different doses of the milk allergen.

13. The method of claim 1, wherein the milk allergen comprises milk proteins.

14. The method of claim 1, wherein step a) further comprises:
    determining the inflammatory reaction of the subject generated by different forms of the milk allergen; and
    selecting a form of milk allergen for the treatment based on said determination.

* * * * *